United States Patent [19]

Wang et al.

[11] Patent Number: 4,859,726
[45] Date of Patent: Aug. 22, 1989

[54] BIS-BENZOTRIAZOLYL COMPOUNDS AND POLYMERIC MATERIALS STABILIZED THEREWITH

[75] Inventors: Richard H. S. Wang; Garry L. Myers, both of Kingsport, Tenn.

[73] Assignee: Eastman Kodak Company, Rochester, N.Y.

[21] Appl. No.: 261,524

[22] Filed: Oct. 24, 1988

[51] Int. Cl.$^4$ .............................................. C08K 5/34
[52] U.S. Cl. ..................... 524/91; 548/259; 548/260
[58] Field of Search ................... 524/91; 548/259, 260

[56] References Cited

U.S. PATENT DOCUMENTS

| | | | |
|---|---|---|---|
| 3,230,194 | 1/1966 | Boyle | 260/45.8 |
| 4,226,763 | 10/1980 | Dexter et al. | 260/45.8 |
| 4,278,589 | 7/1981 | Dexter et al. | 260/45.8 |
| 4,477,614 | 10/1984 | Dexter et al. | 524/91 |
| 4,681,905 | 7/1987 | Kubota et al. | 524/91 |
| 4,684,679 | 8/1987 | Kubota et al. | 524/91 |
| 4,684,680 | 8/1987 | Kubota et al. | 524/91 |
| 4,760,148 | 7/1988 | Seltzer et al. | 524/91 |

FOREIGN PATENT DOCUMENTS

| | | | |
|---|---|---|---|
| 180993 | 7/1985 | European Pat. Off. | |
| 247480 | 12/1987 | European Pat. Off. | 524/91 |
| 47512 | 12/1975 | Japan | 524/91 |

Primary Examiner—John Kight
Assistant Examiner—Kriellian Morgan
Attorney, Agent, or Firm—J. Frederick Thomsen; William P. Heath, Jr.

[57] ABSTRACT

Disclosed are bis-benzotriazolylphenol compounds having the formula

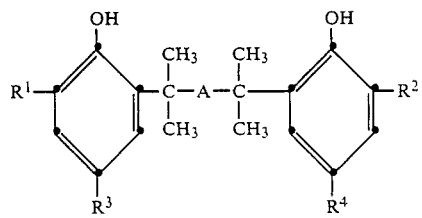

wherein
  $R^1$ and $R^2$ each is a 2-benzotriazolyl radical;
  $R^3$ and $R^4$ each is hydrogen, alkyl, aralkyl, alkoxy, aryl, carboxy, alkoxycarbonyl or halogen; and
  A is 1,3- or 1,4-phenylene.

Also disclosed ae synthetic polymeric materials stabilized with one of the above compounds.

16 Claims, No Drawings

BIS-BENZOTRIAZOLYL COMPOUNDS AND POLYMERIC MATERIALS STABILIZED THEREWITH

DESCRIPTION

This invention concerns certain novel bis-benzotriazolylphenol compounds and polymeric materials stabilized therewith. More specifically, this invention concerns bis[(2-benzotriazolyl)-2-hydroxyphenylpropyl]benzene compounds which exhibit improved resistance to sublimation and or decomposition when used in synthetic, polymeric materials which are subjected to high temperatures during the processing, casting and/or molding thereof.

Various types of synthetic polymeric materials are degraded upon exposure to ultra-violet radiation, i.e., UV light. Many 2-(2-benzotriazolyl)phenol compounds have been incorporated into such polymeric materials to inhibit their degradation by UV light. Examples of such 2-(2-benzotriazolyl)phenol compounds are disclosed in U.S. Pat. Nos. 3,230,194, 4,226,763, 4,278,589 and the patents referred to therein. Bis[(2-benzotriazolyl)-2-hydroxyphenyl]methane compounds and polymeric materials stabilized therewith are disclosed in U.S. Pat. Nos. 4,681,905, 4,684,679 and 4,684,680 and in European patent application 180,993. The ultimate utility of synthetic, polymeric materials may necessitate the exposure of the polymeric material to high temperatures, e.g., during the processing of the polymer when various additives such as fillers, colorants, etc. are blended with or into the polymer and during the molding or shaping of the compounded polymer composition into various articles of commerce. It is therefore desirable if not essential that UV stabilizers possess good stability at high temperatures and resistance to sublimation or volatilization to ensure that shaped articles manufactured from the polymer contain an effective amount of the stabilizer.

The bis-benzotriazolyl compounds provided by this invention have the general formula

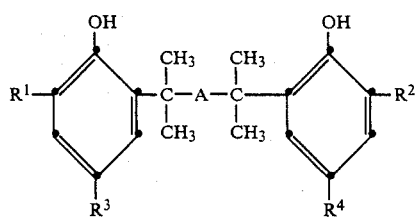

(I)

wherein $R^1$ and $R^2$ each is a 2-benzotriazolyl radical;
$R^3$ and $R^4$ each is hydrogen, alkyl, aralkyl, alkoxy, aryl, carboxy, alkoxycarbonyl or halogen; and
A is 1,3- or 1,4-phenylene.

Examples of the alkyl groups represented by $R^3$ and $R^4$ include alkyl containing up to about 18 carbons such as methyl, ethyl, propyl, 2-propyl, butyl, 2-butyl, 2-methyl-2-propyl, pentyl, 2-pentyl, hexyl, 2-ethylhexyl, 2,4,4-trimethyl-2-pentyl, decyl, dodecyl, hexadecyl and octadecyl. The alkyl groups represented by $R^3$ and $R^4$ preferably contain up to 8 carbon atoms. The alkoxy groups and the alkoxy moiety of the alkoxycarbonyl moiety of the alkoxycarbonyl groups which $R^3$ and $R^4$ can represent may contain up to about 8 carbon atoms and include methoxy, ethoxy, propoxy, butoxy, hexyloxy, octyloxy and isomers thereof. The aryl groups and the aryl moieties of the aralkyl radicals represented by $R^3$ and $R^4$ may be unsubstituted phenyl or phenyl substituted with 1 or 2 groups selected from lower, i.e., containing up to about 4 carbon atoms, alkyl, lower alkoxy or halogen, e.g., chlorine or bromine. The alkyl moiety of the aralkyl groups typically is lower alkyl. Such aralkyl groups preferably are benzyl, 1-phenylethyl and 2-phenyl-2-propyl.

The 2-benzotriazolyl radicals represented by $R^1$ and $R^2$ are well known in the art pertaining to 2-(2-benzotriazolyl)phenols which have been used to inhibit the degradation of polymeric materials upon exposure to UV light. In addition to the patents cited hereinabove, typical 2-benzotriazolyl residues which $R^1$ and $R^2$ may represent are disclosed in U.S. Pat. Nos. 3,004,896, 3,978,074, 4,001,266, 4,041,044 and 4,347,180. Typical of such 2-benzotriazolyl residues are those having the structure:

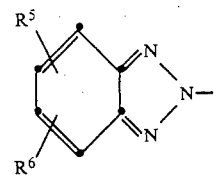

wherein
$R^5$ is hydrogen, alkyl, alkoxy or halogen; and
$R^6$ is hydrogen, alkyl, alkoxy, halogen, hydroxy, carboxy, alkoxycarbonyl, alkylsulfonyl, aryl, aralkyl, aryloxy or aralkoxy. Examples of the groups which $R^5$ and $R^6$ may represent, including the alkyl residue of the alkylsulfonyl group and the aryl and alkoxy moieties of the aryloxy and aralkoxy groups are set forth in the preceding description of $R^3$ and $R^4$. Preferred radicals represented by $R^1$ and $R^2$ are unsubstituted 2-benzotriazolyl and 2-benzotriazolyl substituted with one substituent, preferably at the 5-position, selected from alkyl and chloro.

The compounds of formula (I) may be prepared by conventional procedures utilized heretofore in the preparation of 2-(2-benzotriazolyl)phenol compounds. For example, an o-nitroaniline compound, e.g., having the formula

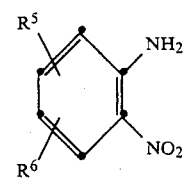

(II)

may be diazotized and the resulting diazonium salt coupled with a bis-phenol having the formula

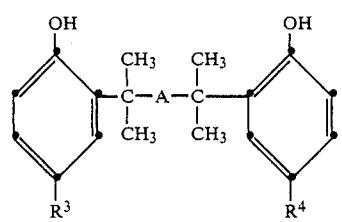

(III)

to obtain a bisazo compound having the formula

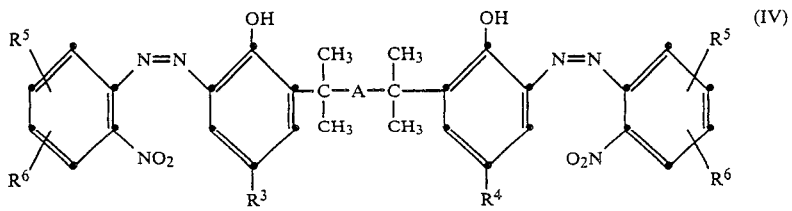

wherein $R^3$, $R^4$, $R^5$, $R^6$ and A are defined above. Bisazo compounds (IV) may then be ring-closed by various procedures to obtain the bis-benzotriazolyl compounds of formula (I).

The bis-phenols of formula (III) are prepared by reacting m- or p-diisopropenylbenzene with phenols having the formula

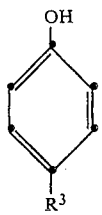

wherein $R^3$ is defined above. Example of phenols (V) include 4-methylphenol, 4(2-methyl-2-butyl)phenol, 4-(2,4,4-trimethyl-2-pentyl)phenol, 4-(2-methyl-2-propyl)phenol, 4-octylphenol, 4-dodecylphenol, 4-methoxyphenol, 4-chlorophenol, 4-methoxycarbonylphenol, 4-(2-phenyl-2-propyl)phenol and 4-(1-phenylethyl)phenol. Additional examples of phenols (V) are given in the patents referred to hereinabove.

The preferred compounds of our invention have the formula

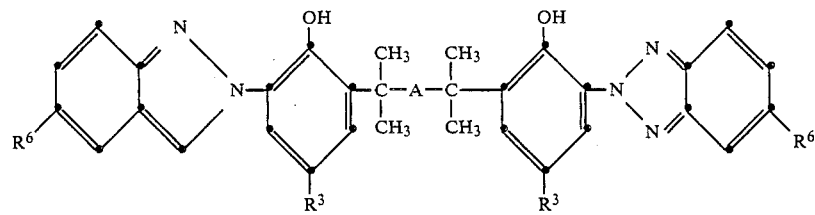

wherein
- $R^3$ is alkyl or alkoxy of up to about 8 carbon atoms, phenylalkyl of 7 to about 9 carbon atoms, chloro or methoxycarbonyl;
- $R^6$ is hydrogen, alkyl of up to about 8 carbon atoms, or chloro; and
- A is 1,3- or 1,4-phenylene.

The bis-benzotriazolyl compounds of formula (I) may be used in a wide variety of synthetic polymeric materials which are susceptible to degradation upon exposure to heat and/or radiation including both visible and ultraviolet light. Examples of such polymeric materials include:

1. Polymers derived from mono- or di-olefins, e.g., polyethylene which optionally may be cross-linked, polypropylene, polyisobutylene, polymethyl-1-butene, polymethyl-1-pentene, polyisoprene, polybutadiene, mixtures of (a) polyethylene and polypropylene, (b) polypropylene and poly-1-butene and (c) polypropylene and polyisobutylene; copolymers of olefins such as ethylene/propylene copolymers, propylene/1-butene copolymers, propylene/isobutylene copolymers, ethylene/1-butene copolymers, and terpolymers of ethylene and propylene with a diene such as hexadiene, dicyclopentadiene, and copolymers of ethylene with acrylic and methacrylic acid.

2. Polymers derived wholly or in part from vinyl aromatic compounds, e.g., polystyrene; styrene/butadiene copolymers; styrene/acrylonitrile copolymers; styrene/acrylonitrile/methacrylate polymers; styrene/acrylonitrile copolymers modified with acrylic ester polymers; styrene/butadiene block copolymers; graft copolymers of styrene such as a graft polymer of styrene to polybutadiene and the graft copolymer of styrene with acrylonitrile to polybutadiene; and acrylonitrile/butadiene/styrene (ABS) polymers.

3. Polymers derived from aliphatic vinyl compounds, e.g., halogen-containing vinyl compounds including polyvinyl chloride, polyvinylidene chloride, polyvinyl fluoride, polychloroprene, chlorinated rubbers, vinyl chloride/vinylidene chloride copolymers, vinyl chloride/vinyl acetate copolymers and vinylidene chloride/vinyl acetate copolymers; $\alpha,\beta$-unsaturated acids and derivatives thereof such as polyacrylates and polymethacrylates, polyacrylamides and polyacrylonitrile; and vinyl esters, completely or partially hydrolyzed polymers of vinyl esters and acetals such as polyvinyl acetate, polyvinyl alcohol, polyvinyl stearate, polyvinyl butyral polyallyl phthalate, and copolymers thereof with other unsaturated monomers such as ethylene/vinyl acetate polymers.

4. Polyalkylene glycols such as polyoxyethylene glycol and polyoxypropylene glycol.

5. Polycarbonates such as those derived from bisphenol A and phosgene.

6. Polyamides and copolyamides derived from diamines and dicarboxylic acids and/or from amino carboxylic acids or the corresponding lactams such as nylon 6, nylon 66, nylon 6/10, nylon 11, nylon 12 and polyphenylene isophthalamide.

7. Polyesters derived from dicarboxylic acids and glycols and/or hydroxycarboxylic acids such as poly(ethylene terephthalate), poly(1,4-cyclohexanedimethanol terephthalate) and poly(tetramethylene terephthalate).

8. Unsaturated polyesters including polyester resins and alkyd resins derived from saturated and unsaturated dicarboxylic acids and/or anhydrides and glycols such as propylene glycol/maleic anhydride/isophthalic acid polyesters which may be cross-linked with another unsaturated compound such as styrene.

The bis-benzotriazolyl compounds provided by this invention are particularly useful as stabilizers in polymeric materials, such as polycarbonates, having high melting points which require high temperatures in the processing, molding and/or extrusion thereof.

The concentration of the bis-benzotriazolyl compound in the polymeric material which will effectively inhibit polymer degradation can vary considerably depending on the particular polymer being stabilized and the end use for which the stabilized polymeric material is designed. Generally, concentration in the range of 0.001 to 5.0 weight percent may be used with concentrations of about 0.01 to 0.5 weight percent being most common for most polymeric materials. However, when the polymeric material is to be used in manufacturing coatings, films or other relatively thin materials, the concentration of the bis-benzotriazolyl compound typically is in the range of about 0.1 to 1.0 weight percent. The bis-benzotriazolyl stabilizers provided by this invention typically will be used in combination with other conventional stabilizers such as phenolic antioxidants, polyvalent salts of organic acids, organic phosphites, hindered amine light stabilizers and thioethers. In addition, other additives, such as plasticizers, lubricants, emulsifiers, antistatic agents, flame retardant agents, pigments and fillers, commonly used in formulating commercial polymeric compositions may be present.

The bis-benzotriazolyl compounds may be incorporated into the polymeric materials by conventional blending techniques. For example, the stabilizer may be added directly to a melt of the polymer on a roll mill to distribute the compound uniformly throughout the polymer. Alternatively, the bis-benzotriazolyl compound may be dry-blended with a finely-divided form of the polymer such as pellets and then the dry mix can be mixed further in and extruded from an extruder. Another compounding method which may be used comprises mixing a solution or suspension of the stabilizer with a solution, suspension or emulsion of the polymeric material.

Our invention is further illustrated by the following examples.

EXAMPLE 1

A mixture of aluminum powder (0.02 mol) and p-cresol (0.22 mol) is heated at 150° C. for 1 hour. After cooling the mixture to 120° C., 1,3-diisopropenylbenzene (0.1 mol) is added over a 30-minute period. The reaction mixture then is heated at 120° C. for 4 hours and at 150° C. for 1 hour. After cooling the mixture to room temperature, acetone (500 mL) is added and the remaining insoluble material is removed by filtration. The acetone is removed and heptane (500 mL) added to precipitate the product, 1,3-bis[2-(2-hydroxy-5-methylphenyl)-2-propyl]benzene, m.p. 160°–5° C., which is isolated in an 80% yield by filtration.

To a solution of 2-nitroaniline (0.4 mol) in 800 mL of propionic/acetic acid mixture (1:5 by volume) at 0°–5° C. is added nitrosylsulfonic acid (0.4 mol) in 74 g of 98% sulfuric acid. At −5°–0° C., a solution of the bisphenol (0.1 mol) prepared above in 40 mL pyridine is added slowly over a period of 30 minutes. The pH of the mixture is then adjusted to 4.5 by adding 300 g of ammonium sulfate and the mixture is stirred for 2 hours at −5°–0° C. The mixture then is poured into 1 L of water and the product is isolated by filtration, washed with hot water and dried to give a quantitative yield of 1,3-bis[2-[3-(2-nitrophenylazo)-2-hydroxy-5-methylphenyl]-2-propyl]benzene. Mass spectroscopy analysis (FDMS=672) supports the structure of the product.

To a stirred, refluxing mixture of the above bisazo compound (0.1 mol) in 750 mL is added sodium hydroxide (2.1 mol) in 300 ml of water. A slurry of zinc powder (1.0 mol) in 250 mL ethanol then is added slowly and the mixture is heated at reflux for 5 hours. Some insoluble material is removed by filtration and the filtrate is added to a solution of 200 mL of 36% hydrochloric acid in 1800 mL of water with stirring. The resulting solids are separated by filtration and dried to give 52 g of crude product. After extraction through a Soxhlet extractor with heptane, 15 g of pure product (m.p. 202° C.) are obtained. Mass spectroscopy analysis (FDMS=608) and ultraviolet/visible spectra confirm that the product has the structure expected:

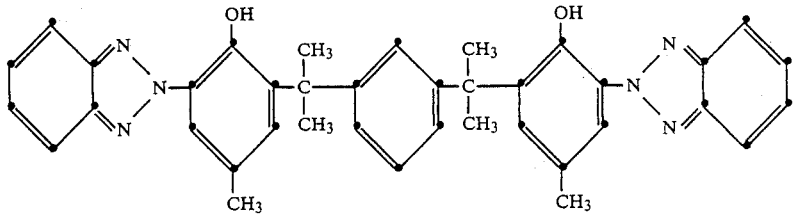

UV/VIS(CH$_2$C$_{12}$): λmax 290 nm (27,950) and 333 nm (ε27,600)

The thermal stability and/or volatility of the bis-benzotriazolyl compound (A) of Example 1 and that of a known stabilizer, 2-(2-benzotriazolyl)-4,6-bis(2-phenyl-2-propyl)phenol sold under the name Tinuvin 234, is determined by thermogravimetric analysis (TGA) in a 951 Thermogravimetric Analyzer wherein 5–15 mg samples of Compounds A and B are heated from 20° to 600° C. at a heat-up rate of 20° C. per minute in a nitrogen atmosphere. The weight percent loss of each sample is recorded as the heater temperature rises.

The sample of compound A loses 5% of its weight after being heated to a maximum of 350° C. and loses 10% of its weight after being heated to a maximum of 370° C. In contrast, known stabilizer B loses 5% of its weight after being heated to a maximum temperature of only 300° C. and 10% of its weight after being heated to a maximum temperature of 315° C.

The specific absorptivity, determined by dividing the molar extinction coefficient (ε) by molecular weight, of Compound A is 46 at 290 nm and 45 at 323 nm whereas the specific absorptivity of Compound B is 35 at 290 nm and 37 at 323 nm. Spefific absorptivity is the magnitude of the intensity of light absorption by a unit weight of a compound and is an indication of the relative effectiveness of a compound as a light stabilizer: the greater the specific absorptivity, the greater the stabilizer effectiveness.

The compounds set forth in Table I conform to the formula

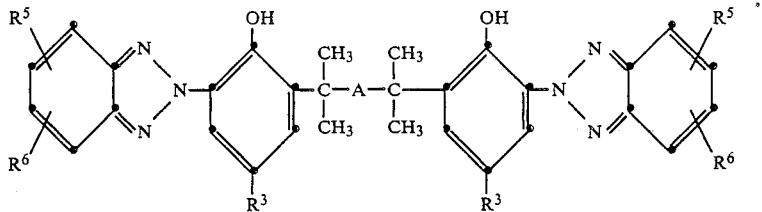

wherein A is a phenylene residue, either 1,3- or 1,4- as indicated. These compounds are prepared from the appropriate o-nitroaniline compound (II), phenol (V) and diisopropenylbenzene according to the procedure described in Example 1.

TABLE I

| Example | R⁵, R⁶ | A | R² |
| --- | --- | --- | --- |
| 2 | H | 1,3- | H |
| 3 | H | 1,3- | C₆H₅CH(CH₃)— |
| 4 | H | 1,3- | (CH₃)₃C— |
| 5 | H | 1,3- | (CH₃)₃CCH₂C(CH₃)₂— |
| 6 | H | 1,3- | CH₃O— |
| 7 | 5-SO₃H | 1,3- | CH₃— |
| 8 | 5-COOC₂H₅ | 1,3- | CH₃— |
| 9 | 5-Cl | 1,3- | CH₃— |
| 10 | H | 1,4- | CH₃— |
| 11 | H | 1,4- | CH₃O— |
| 12 | 5,6-di-CH₃ | 1,4- | Cl |

Stabilizer Compound A is evaluated as stabilizer in a polycarbonate derived from bisphenol A and phosgene, sold under the name Markalon Polycarbonate 2600 by Mobay Chemical Company, and having a density of 0.0433, a specific volume of 23.1 and a melt flow rate of 11 g/10 minutes. A solution (or dispersion if not completely dissovled) of the stabilizer compound in approximately 50 mL of acetone is poured over the polycarbonate granulated to pass a 3 mm screen in an amount sufficient to give a stabilizer concentration of 0.5 weight percent based on the weight of the polycarbonate. The mixture is stirred vigorously with a spatula until most of the acetone has evaporated. The polycarbonate-stabilizer mixture then is dried in air for about 2 hours and then in a vacuum oven at 120° C. for 16 hours. The mixture then is blended and pelletized using a Brabender extruder (320° C.) with a mixing screw. The pellets are dried as described above and injection molded into test bars ½ inch×2-½ inch×⅛ inch thick using a Boy 225 injection molding machine (300° C.).

The Gardner CDM color (b value), flatwise impact strength (FWIS, ASTM D4508) tensile strength (ASTM-D638) and elongation (ASTM-D638) are measured for the test bars molded from the polycarbonate containing no stabilizer compound and from the polycarbonate containing Compound A. The sample bars are then exposed to weathering for 500 hours in an Atlas XWR Weather-Ometer (carbon arc) and the same values are again determined. The above-described values, determined initially and after weathering exposure, are set forth in Table II.

TABLE II

| Stabilizer Compound | Gardner Color | FWIS | Tensile Strength | Elongation |
| --- | --- | --- | --- | --- |
| None - Initial | 4.0 | 18.30 | 13.42 | 97% |
| None - Exposed | 11.1 | 19.14 | 10.04 | 66% |
| A - Initial | 6.8 | 19.26 | 10.52 | 76% |
| A - Exposed | 9.6 | 22.21 | 10.91 | 75% |

Test bars molded as described above from the polycarbonate containing no stabilizer or Compound A are exposed in a Q-U-V Weathering device (UV-B-λmax 313 nm) and the physical properties of each test bar are detemined as for the Table II data after 500 hours and again after 1000 hours exposure. The values determined are set forth in Table III.

TABLE III

| Stabilizer Compound | Gardner Color | FWIS | Tensile Strength | Elongation |
| --- | --- | --- | --- | --- |
| None - Initial | 4.0 | 18.30 | 13.42 | 97% |
| None - Exposed | | | | |
| 500 hours | 22.4 | 11.33 | 9.28 | 45% |
| 1000 hours | 21.8 | 8.91 | 8.77 | 19% |
| A - Initial | 6.8 | 19.26 | 10.52 | 76% |
| A - Exposed | | | | |
| 500 hours | 14.9 | 21.69 | 9.85 | 55% |
| 1000 hours | 16.2 | 22.37 | 9.11 | 56% |

The invention has been described in detail with particular reference to preferred embodiments thereof, but it will be understood that variations and modifications will be effected within the spirit and scope of the invention.

We claim:

1. A compound having the formula

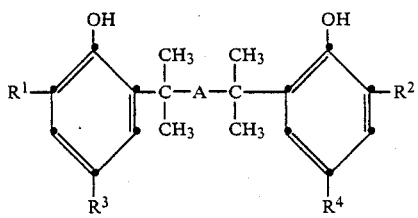

wherein
R¹ and R² each is a 2-benzotriazolyl radical:
R³ and R⁴ each is hydrogen, alkyl, aralkyl, alkoxy, aryl, carboxy, alkoxycarbonyl or halogen; and
A is 1,3- or 1,4-phenylene.

2. A compound according to claim 1 wherein R¹ and R² each is a 2-benzotriazolyl radical having the formula

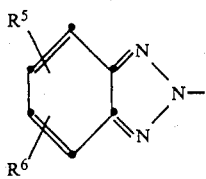

wherein
R⁵ is hydrogen, alkyl, alkoxy or halogen; and
R⁶ is hydrogen, alkyl, alkoxy, halogen, hydroxy, carboxy, alkoxycarbonyl, alkylsulfonyl, aryl, aralkyl, aryloxy or aralkoxy.

3. A compound according to claim 1 having the formula

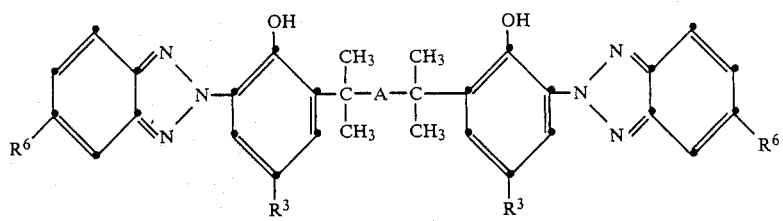

wherein
R³ is alkyl or alkoxy of up to about 8 carbon atoms, phenylalkyl of 7 to about 9 carbon atoms, chloro or methoxycarbonyl;
R⁶ is hydrogen, alkyl of up to about 8 carbon atoms, or chloro; and
A is 1,3- or 1,4-phenylene.

4. A compound according to claim 1 having the formula

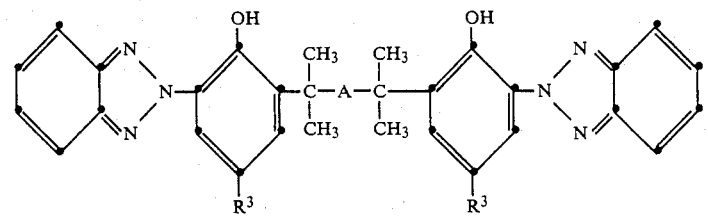

wherein R³ is lower alkyl and A is 1,3- or 1,4-phenylene.

5. A stabilized composition comprising a synthetic polymeric material susceptible to degradation upon exposure to heat and/or radiation containing a stabilizing amount of a compound defined in claim 1.

6. A stabilized composition comprising a synthetic polymeric material susceptible to degradation upon exposure to heat and or radiation containing a stabilizing amount of a compound defined in claim 2.

7. A stabilized composition comprising a synthetic polymeric material susceptible to degradation upon exposure to heat and/or radiation containing about 0.01 to 0.5 weight percent based on the weight of the polymeric material of a compound defined in claim 1.

8. A stabilized composition comprising a synthetic polymeric material susceptible to degradation upon exposure to heat and/or radiation containing about 0.01 to 0.5 weight percent based on the weight of the polymeric material of a compound defined in claim 2.

9. A stabilized composition comprising a synthetic polymeric material susceptible to degradation upon exposure to heat and/or radiation containing about 0.01 to 0.5 weight percent based on the weight of the polymeric material of a compound defined in claim 3.

10. A stabilized composition according to claim 5 wherein the polymeric material is an α-olefin homo- or co-polymer.

11. A stabilized composition according to claim 5 wherein the polymeric material is polypropylene.

12. A stabilized composition comprising an α-olefin homo- or co-polymer containing from about 0.01 to 0.05 weight percent based on the weight of the α-olefin polymer of a compound defined in claim 2.

13. A stabilized composition comprising an α-olefin homo- or co-polymer containing from about 0.01 to 0.05 weight percent based on the weight of the α-olefin polymer of a compound defined in claim 3.

14. A stabilized composition comprising a polycarbonate polymer containing a stabilizing amount of a compound defined in claim 1.

15. A stabilized composition comprising a polycarbonate polymer containing a stabilizing amount of a compound define in claim 3.

16. A stabilized composition comprising a polycarbonate polymer derived from bisphenol A containing about 0.1 to 1.0 weight percent based on the weight of the polymer of a compound defined in claim 3.

* * * * *